(12) United States Patent
Pusch et al.

(10) Patent No.: US 10,881,533 B2
(45) Date of Patent: Jan. 5, 2021

(54) PROSTHETIC FOOT INCLUDING A HEEL CAP AND INTERCHANGEABLE HEEL-SIDE SPRING-DAMPER

(71) Applicant: OTTO BOCK HEALTHCARE GMBH, Duderstadt (DE)

(72) Inventors: Martin Pusch, Duderstadt (DE); Jens Noerthemann, Duderstadt (DE); Darshan Rane, Milcreek, UT (US); Carsten Moenicke, Duderstadt (DE); Nathan Aaron Williams, Meriden, WY (US)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 0 days.

(21) Appl. No.: 15/305,633

(22) PCT Filed: May 6, 2015

(86) PCT No.: PCT/EP2015/000926
§ 371 (c)(1),
(2) Date: Oct. 20, 2016

(87) PCT Pub. No.: WO2015/169443
PCT Pub. Date: Nov. 12, 2015

(65) Prior Publication Data
US 2017/0049584 A1    Feb. 23, 2017

(30) Foreign Application Priority Data
May 7, 2014    (DE) .......... 10 2014 006 571

(51) Int. Cl.
*A61F 2/66* (2006.01)
*A61F 2/50* (2006.01)

(52) U.S. Cl.
CPC ........ *A61F 2/66* (2013.01); *A61F 2002/5007* (2013.01); *A61F 2002/5072* (2013.01);
(Continued)

(58) Field of Classification Search
CPC ............. A61F 2/60; A61F 2/66; A61F 2/6607
See application file for complete search history.

(56) References Cited

U.S. PATENT DOCUMENTS

| | | | | |
|---|---|---|---|---|
| 5,037,444 A | * | 8/1991 | Phillips | A61F 2/66 623/53 |
| 5,139,525 A | | 8/1992 | Kristinsson | |

(Continued)

FOREIGN PATENT DOCUMENTS

| | | |
|---|---|---|
| CA | 2253631 A1 | 9/1998 |
| CN | 1219116 A | 6/1999 |

(Continued)

OTHER PUBLICATIONS

Endolite, Blade XT, Chas A Blatchford & Sons Ltd., 2 pages (no date).

(Continued)

*Primary Examiner* — Marcia L Watkins
(74) *Attorney, Agent, or Firm* — Holland & Hart LLP

(57) ABSTRACT

A prosthetic foot with a structural component having a proximal attachment member for fastening the prosthetic foot to a below-knee tube, a below-knee shaft or a prosthetic knee joint, with a forefoot portion secured or formed on the structural component, and with a heel-side spring-damper system which is assigned to the structural component and which is compressed at a heel strike and bears on a sole-side guide element. The structural component is designed as a leaf spring which extends in a posterior direction from the proximal attachment means, and forms an arch and is guided (Continued)

in an anterior and distal direction, wherein the arch protrudes posteriorly beyond the guide element.

25 Claims, 18 Drawing Sheets

(52) U.S. Cl.
CPC . *A61F 2002/665* (2013.01); *A61F 2002/6657* (2013.01); *A61F 2002/6671* (2013.01)

(56) References Cited

U.S. PATENT DOCUMENTS

| | | | | |
|---|---|---|---|---|
| 5,593,456 | A * | 1/1997 | Merlette | A61F 2/60 623/32 |
| 6,241,776 | B1 * | 6/2001 | Christensen | A61F 2/66 623/52 |
| 6,514,293 | B1 | 2/2003 | Jang et al. | |
| 6,719,807 | B2 | 4/2004 | Harris | |
| 7,172,630 | B2 | 2/2007 | Christensen | |
| 8,317,876 | B2 | 11/2012 | Mosler | |
| 8,535,390 | B1 | 9/2013 | Lecomte et al. | |
| 8,771,372 | B1 * | 7/2014 | Rubie | A61F 2/66 623/52 |
| 9,486,331 | B2 | 11/2016 | Friesen et al. | |
| 2003/0191541 | A1 * | 10/2003 | Phillips | A61F 2/66 623/55 |
| 2004/0068327 | A1 | 4/2004 | Christensen | |
| 2004/0162623 | A1 | 8/2004 | Phillips | |
| 2005/0033450 | A1 | 2/2005 | Christensen | |
| 2005/0038524 | A1 | 2/2005 | Jonsson et al. | |
| 2006/0069450 | A1 * | 3/2006 | McCarvill | A61F 2/66 623/55 |
| 2007/0061016 | A1 | 3/2007 | Kuo et al. | |
| 2008/0167731 | A1 | 7/2008 | Christensen et al. | |
| 2009/0012630 | A1 * | 1/2009 | Mosler | A61F 2/66 623/55 |
| 2010/0023135 | A1 | 1/2010 | Rubie et al. | |
| 2012/0046760 | A1 | 2/2012 | Nissels et al. | |
| 2012/0179274 | A1 | 7/2012 | Christensen | |
| 2012/0209405 | A1 | 8/2012 | Herr et al. | |
| 2012/0271434 | A1 * | 10/2012 | Friesen | A61F 2/66 623/55 |
| 2012/0303135 | A1 * | 11/2012 | Vo | A61F 2/60 623/33 |
| 2013/0144403 | A1 | 6/2013 | Lecomte et al. | |
| 2014/0012397 | A1 * | 1/2014 | Mosler | A61F 2/66 623/55 |
| 2014/0046456 | A1 | 2/2014 | Smith et al. | |

FOREIGN PATENT DOCUMENTS

| | | |
|---|---|---|
| CN | 1514703 A | 7/2004 |
| CN | 102665614 A | 9/2012 |
| EP | 2420212 A1 | 2/2012 |
| JP | 2001-276102 A | 10/2001 |
| JP | 2002-504007 A | 2/2002 |
| JP | 2007-502629 A | 2/2007 |
| JP | 2009-520526 A | 5/2009 |
| JP | 2013-512043 A | 4/2013 |
| RU | 2137443 C1 | 9/1999 |
| RU | 2157152 C1 | 10/2000 |
| WO | 2012009319 A2 | 1/2012 |

OTHER PUBLICATIONS

PCT International Search Report for PCT International Patent Application No. PCT/EP2015/000926, dated Jul. 23, 2015.

* cited by examiner

PROSTHETIC FOOT INCLUDING A HEEL CAP AND INTERCHANGEABLE HEEL-SIDE SPRING-DAMPER

TECHNICAL FIELD

The invention relates to a prosthetic foot comprising a structural component with proximal connection means for fastening the prosthetic foot to a below knee tube, below knee shank or a prosthetic knee joint, a forefoot portion fastened to, or embodied at, the structural component and a heel-side spring-damper system assigned to the structural component, said spring-damper system being compressed at a heel strike and supporting itself on a sole-side guide element. The prosthetic foot is also suitable for arrangement in a shoe and embodied to this end.

BACKGROUND

Prosthetic feet serve as distal termination for a prosthetic device and can be fixed to a below knee tube, which is fastened to a prosthetic knee joint, directly to a prosthetic shank or to the prosthetic knee joint. To this end, connection means are regularly provided at the proximal end on the prosthetic foot in order to establish a stable and permanent connection with the proximal prosthetic component. Prosthetic feet are usually provided with cosmetic means, which consist of plastic and are embodied approximately in the form of a natural foot.

From the structural point of view, the simplest form of a prosthetic foot is a rigid foot; however, it has significant disadvantages in view of the elastic properties or the rollover properties.

Damper elements or heel springs may be provided for damping the momentum upon heel strike; it is likewise possible for a spring to be arranged in the forefoot region in order to ease the rollover of the foot over the whole stance phase and, moreover, to re-emit the deformation energy, previously taken-in, in the terminal stance phase so as to assist the prosthetic foot user when walking.

U.S. Pat. No. 7,172,630 B2 relates to a prosthetic foot comprising two leaf spring elements which are coupled to one another in the forefoot region. A cam which presses against a tension spring is arranged at one leaf spring. It is possible to tension or relax the tension spring by displacing the cam such that a specific force profile can be realized over the heel-toe movement.

U.S. Pat. No. 5,139,525 A relates to a prosthetic foot with an articulated receptacle for a below knee tube. The articulated receptacle is arranged in the region of the natural ankle joint. The spring characteristic of the prosthetic foot can change over the course of a heel-toe movement.

US 2007/0061016 A1 relates to a prosthetic foot with a heel plate and a toe plate which are connected to one another in an articulated manner, swivelable about a central axis. A spring is arranged between the heel plate and the toe plate and supports itself at a rearward extension of the toe plate. An adapter plate is likewise arranged in a manner swivelable about the central axis. The energy arising when walking is actively stored and re-emitted by way of sensor devices.

U.S. Pat. No. 6,719,807 B2 relates to a prosthetic foot comprising a wavelike-contoured forefoot spring and a heel spring, which is fastened in the midfoot region, extends backward and is arranged in a cosmetic foot covering. Forefoot spring and heel spring are mounted in a frame. A variant provides for the heel spring to be connected to the forefoot spring by way of a base spring which is fastened, firstly, to the posterior end of the heel spring and, secondly, to the forefoot spring in the midfoot region.

US 2012/0046760 A1 relates to a prosthetic foot comprising an integral spring which comprises a lower base portion and an upper part rising upward in an arcuate manner. The base portion and upper part are provided with a longitudinal slot in the forefoot region; a damper made of an elastomeric material is arranged in the heel region.

US 2014/0046456 A1 relates to a prosthetic foot comprising a planar base spring, an arcuate forefoot spring with a connection adapter fastened thereto and a damper element which supports the base spring against the forefoot spring in the region of the heel.

A prosthetic foot for amateur athletes and runners is distributed by Chas A Blatchford & Sons Ltd. under the trade name "endolite Blade XT"; it comprises a forefoot spring comprising a substantially horizontal head portion and an integral spring with an outwardly convex form, said spring being divided into two in the lower region by a slit. In the front region of the spring, a sole protection and a heel spring are fastened by way of two screws; the spring stiffness of the heel spring can be set by way of a wedge. The heel spring has a less flexible reaction as a consequence of inserting the heel wedge.

SUMMARY

It is an object of the present invention to provide a prosthetic foot which has a simple design, simplifies walking for a prosthetic foot user and, in particular, is advantageously usable in the case of sports activities.

According to the invention, this object is achieved by a prosthetic foot having the features of the main claim. Advantageous refinements and developments of the invention are disclosed in the dependent claims, description and the figures.

The prosthetic foot according to the invention comprising a structural component with proximal connection means for fastening the prosthetic foot to a below knee tube, a below knee shank or a prosthetic knee joint, a forefoot portion fastened to, or embodied at, the structural component and a heel-side spring-damper system assigned to the structural component, said spring-damper system being compressed at a heel strike and supporting itself on a sole-side guide element, provides for the structural component to be embodied as a leaf spring, which extends from the proximal connection means in the posterior direction, forms an arc and is guided in the anterior and distal directions, with the arc projecting beyond the guide element in the posterior direction. As a result of the heel-side spring-damper system, which is connected to the support structure by way of the guide element, it is possible to enable guidance of the displacement movement of the spring-damper system and of the guide element assigned to the spring-damper system when the heel is loaded. As a result, a pronation and supination movement during impact is at least reduced, as a result of which more precise guidance of the prosthetic foot can be realized during walking. Moreover, there is a transfer of the energy stored in the spring-damper system to the structural component during the rollover from the heel to the forefoot by virtue of the spring-damper system relaxing, releasing energy and, as a result, bringing about a delay of a deformation of the structural component. As a result of embodying the structural component as a leaf spring, it is possible to store the energy taken up during walking, in particular during running, and provide a long deformation path such that a large energy storage capability during the stance phase can be provided. As a result of the arc projecting beyond the guide element toward the rear, there is significant lengthening of the effective spring length, and so a high degree of deformation and deformability of the structural component in the form of the leaf spring is provided. Moreover, the arc renders it possible to obtain a low prosthetic foot height despite a long effective spring length and, at the same time, the wearability in the shoe is ensured as a result of the rearward projection in the region of the natural ankle joint.

The arc of the structural component projects beyond the natural ankle position in the posterior direction and is arranged approximately level with the natural ankle position, or going slightly therebeyond, such that the apex of the arc lies behind the posterior, rear end of the guide element. The guide element is advantageously arranged at the lower side of the spring-damper system and, as a leaf spring in the forefoot portion of the structural component, fixedly mounted thereon. Here, the guide element is advantageously embodied to be thinner than the leaf spring of the structural component with the forefoot portion, can optionally be embodied as leaf spring or integrally formed on the structural component, in order to reduce pretension of the forefoot portion during a heel strike where possible. As a result of the thin embodiment of the guide element, a greater deformability during a heel strike is ensured such that only a low force component and energy influx is introduced into the forefoot portion. The guide element can be mounted at the support structure with free movement or virtually free movement about an axis oriented transversely to the longitudinal extent of the prosthetic foot, for example by virtue of a type of hinge being embodied in the guide element. Here, an axis is not understood to mean a rail element but rather an imaginary line, at which components can be swiveled in relation to one another. By way of example, an axis is also present if a film hinge, an elastomeric element or a polycentric bearing is provided, by means of which two components are coupled to one another. For the purposes of forming a swivel axis, the guide element can have a film hinge which, firstly, enables folding-like swiveling about a horizontal axis but, secondly, prevents or reduces torsion about the longitudinal axis of the foot and the vertical axis of the foot.

The guide element can be borne directly at the structural component such that the axis, about which the guide element or parts of the guide element is/are freely movable or virtually freely movable, is set directly at the support structure or embodied by the guide element.

In addition to the embodiment of the guide element as a leaf spring, the former can also have a lug-like or folding-like embodiment, as a result of which an introduction of force into the forefoot portion is reduced further.

The spring-damper system is advantageously embodied as a foam-material element or an elastomeric element, as a result of which it is possible to provide a multiplicity of forms, each having a different spring-damper characteristic, using cost-effective materials, and so it is easily possible to adapt the prosthetic foot to the desires or requirements of the prosthetic foot user. It is also possible to easily realize different heel heights. It is possible to set desired spring and damping properties in a cost-effective manner by way of a material mixture. As a result of embodying the spring-damper system as a foam-material element or elastomeric element, it is possible to build up only small shearing forces, or no shearing forces, and so no tensile forces or pressure forces are introduced into the guide element. Advantageously, the spring-damper element supports itself at the lower side of the structural component in the region of the natural ankle, advantageously in a region at which the arc starts such that there is support in the case of a support in the transition from the arc to the forefoot portion. This furthermore prevents there being an energy influx into the forefoot portion during the heel strike.

The spring-damper system can be reversibly arranged between the lower side of the support structure and the upper side of the guide element, for example by way of a holder which is fastened, preferably adhesively bonded, to the lower side of the structural component, into which holder the spring-damper system made of a foam-material element or an elastomeric element can be inserted with form fit. A form-fit element can likewise be arranged at the upper side of the guide element such that an adaptation to the desired stiffness or a replacement during servicing works can take place by simple insertion and latching of the spring-damper system.

The guide element is advantageously embodied as a lug or flap and can be embodied from a metal, in particular a light metal, or a plastics material. Here, the swivel axis, at which the guide element in the form of a lug or flap is mounted, adjoins the support structure such that a relatively long length can be realized for the guide element, as a result of which the spring-damper system can be set in a precise fashion.

A sole element made of an elastic material can be arranged at the lower side of the guide element, said sole element providing an additional spring and additional damping by way of the geometric dimensions and rigidity properties thereof such that the spring-damper system between the support structure and the guide element is not the only resilient element. As a result of the inherent elasticity of the sole element, it is possible to avoid and damp a sudden load uptake and load transfer onto the spring-damper system.

Arranged on the lower side of the guide element there can be a sole element made of an elastic material which, as a result of the geometric dimensions and stiffness properties thereof, is embodied in such a way that the COP (center of pressure) or point of attack of the force remains in the heel region for as long as possible during the rollover in order to avoid premature charging or a deformation of the forefoot spring.

The forefoot portion can be rigidly fastened to the structural component and it is advantageously embodied as a leaf spring or has at least one leaf spring or leaf-spring element. As a result of the rigid attachment to the support structure, it is possible to achieve precise guidance of the forefoot portion, as a result of which it is easier to control the prosthetic foot when walking. The embodiment of the forefoot portion as the spring renders it possible to take up energy when walking. Moreover, it is possible, after the strike with the forefoot portion after the heel strike, to transfer the stored energy from the spring-damper element to the forefoot, with the overall height of the prosthetic foot remaining constant, and so the force guidance is brought about via the floor or the sole structure. The energy stored in the spring-damper element is then emitted by way of the forefoot portion and eases the pushoff of the user at the end of the stance phase.

An overload stop can be arranged between the guide element and the support structure in order to prevent too great compression of the spring-damper system in the case of a massive energy influx, wherein an instability may arise during walking as a result of said too great compression.

The guide element can be mounted in a non-displaceable manner about an axis extending in the anterior-posterior direction and/or about an axis extending in the proximal-distal direction such that the guide element cannot carry out an avoidance movement and, in particular, supination and pronation of the guide element after the strike is prevented. The rigid mount about an axis extending in the anterior-posterior direction prevents the heel of the prosthetic foot bending away laterally when walking, which is advantageous, particularly when used as a foot for sports.

A heel in the proximal direction or convex arching can be embodied at the free end of the guide element in order to enable easy rollover and an adaptation of the sole structure, for example to the body weight or the gait of the patient.

The structural component itself can have an elastic embodiment, in particular an integral or single-piece embodiment such that a continuous leaf spring emerges from the proximal connection means up to the front end of the structural component, in particular up to the front end of the prosthetic foot.

A form-fit element for fixing the spring-damper system can be fixed in each case at the posterior end of the guide element and at the lower side of the structural component; in particular, the form-fit elements are adhesively bonded thereon. The form-fit element arranged at the guide element can be embodied as a rear sole structure that is a heel cap and as a posterior, lower termination of the prosthetic foot and, at the same time, provide damping or cushioning in the heel region and a profile, to the extent that the prosthetic foot should not be worn in a shoe, such that risk of slipping prior to putting on the shoe is reduced. The upper form-fit element for form-fit locking to the lower side of the structural component can also be fixed or securely screwed thereon such that there can be simple assembly and the assembly of the spring-damper system, which can have an integral embodiment and consist of different materials.

The arc of the structural component projecting beyond the guide element toward the back projects beyond the spring-damper system in the anterior-posterior direction by a section which is between 10% and 30%, especially preferably between 12.5% and 25%, of the foot length. Here, the foot length is that length of the prosthetic foot which is measured from the front, anterior end to the rear, posterior end of the guide element, possibly to the rear end of the form-fit element arranged at the guide element.

Contour-forming cushioning can be arranged at the upper side of the structural component in the forefoot region, as a result of which cushioning it is possible to fill a shoe, into which the prosthetic foot is inserted, in a shape-forming manner. Hence, it is not necessary for further cosmetic coverings to be arranged around the prosthetic foot. Rather, the prosthetic foot according to the invention can be worn directly in a shoe.

In a development of the invention, provision is made for a sole to be fastened to the prosthetic foot such that the latter can also be worn without a shoe.

From the proximal connection means, the structural component extends with concave curvature in the arc, convex curvature is present in the region of the support of the spring-damper system at the lower side of the structural component, said convex curvature advantageously having a larger radius of curvature compared to the arc. The convex region of curvature is in turn adjoined by concave curvature in the forefoot portion, wherein the perception of the structural component, proceeding from a top view in the region of the proximal connection means on the original surface, remains over the course from the upper connection means to the tip of the foot, i.e. initially looking from top to bottom and, after the end of the arc, looking from the bottom to the top.

The guide element can be embodied as a leaf spring with a form extending from the heel to the tip of the foot in a concave, convex, concave manner in order, firstly, to reproduce the natural arching of the foot and, secondly, to ensure soft rollover after the heel strike, high elasticity as a result of the convex movement in the midfoot region and soft strike and rollover in the forefoot region. Here, the perception is from the lower side of the guide element.

A development of the invention provides for the forefoot portion and the guide element to be assigned to one another by way of an alignment device. The alignment device simultaneously provides a form for an adhesive connection and, moreover, protection for the components from external influences or for the shoe from possibly sharp-edged leaf springs since the alignment device is adhesively bonded together with the structural component and the guide element and remains at the prosthetic foot.

The forefoot portion, the guide element and the alignment device can be adhesively bonded to one another and, as a result thereof, permanently fastened to one another.

The prosthetic foot is embodied and suitable for arrangement in a shoe, in particular as a result of the embodiment of the structural component with the rearward extended arc in the region of, or above, the natural ankle position and the guide element which assumes a sole function during the stance phase.

BRIEF DESCRIPTION OF THE DRAWINGS

Below, an exemplary embodiment of the invention is explained in more detail on the basis of the figures. In detail.

DETAILED DESCRIPTION

Figure 1:
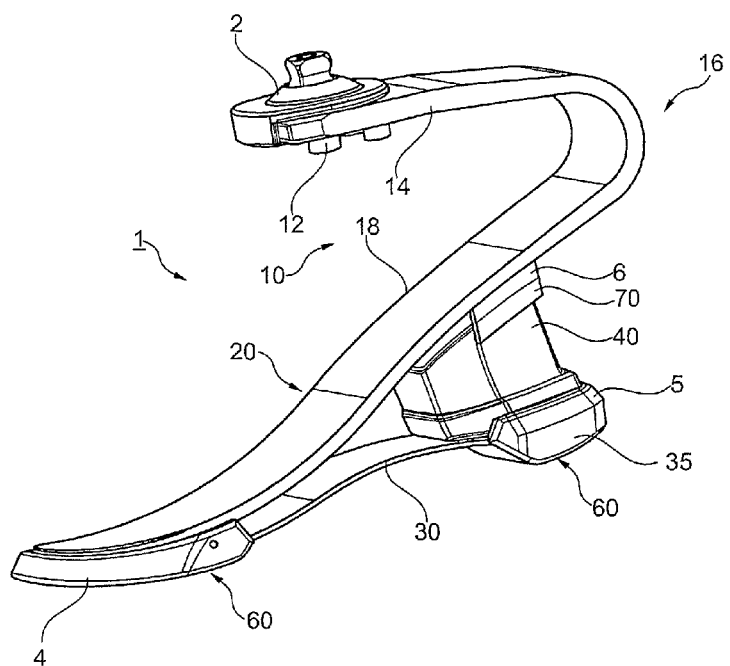
FIG. 1 shows a perspective view of a prosthetic foot.

FIG. 1 shows, in a perspective side view, a prosthetic foot 1 comprising a structural component 10 in the form of an integral leaf spring, at the proximal end of which connection means 2 in the form of an adapter pylon are fastened by way of screws. Screwing is carried out in a support portion 14, which is directed out substantially horizontally and level in the case of a usual setting of the prosthetic foot 1. From the connection means 2, the structural component 10 extends rearward in an arc 16, which is oriented in the posterior direction, with convex curvature in order then to extend in the anterior direction in a connection portion 18 with a concave embodiment. The concave connection portion 18 is adjoined by a forefoot portion 20, once again with a convex shape, which extends into the toe region of the prosthetic foot 1.

An alignment device 4 in the form of a cap is adhesively bonded to the toe region and has a sole element 60 at the lower side thereof, or at the lower side of which a sole element 60 is formed. The alignment device 4 serves, firstly, for receiving and fastening the forefoot portion 20 of the structural component 10, the protection thereof at the front end and at the side edges, and for an alignment in relation to a guide element 30, which is fixed below the forefoot portion 20, and at a distance thereto, at the alignment device. The manner of the fastening and the embodiment of the alignment device 4 are explained in more detail below.

The guide element 30 extends substantially horizontally in the posterior direction, with the guide element 30 being embodied as a leaf spring which, extending from front to rear, has a convex, concave and then convex contour profile again. Arranged at the posterior end of the guide element 30 is a form-fit element 5 in the form of a rear sole structure that is a heel cap, at the lower side of which a sole structure 60 is likewise arranged or formed. The form-fit element 5 can be fixed to the guide element 30 in a form-fit manner, for example by being plugged on, clipped on or screwed on; alternatively, or additionally, it is possible for adhesive bonding and/or welding to be carried out with the guide element 30.

Arranged at the lower side of the structural component 10 in the region of the connection portion 18 is a second form-fit element 6, which is advantageously adhesively bonded, welded or fastened thereon by form-fit elements such as screws or the like. Together with the first form-fit element 5, the second form-fit element 6 serves for reversible reception of a spring-damper system in the form of a foam-material body or of an elastomeric element which is used between the structural component 10 and the guide element 30. To this end, the guide element 30 is moved away from the structural component 10, the spring-damper system 40 is inserted into the increasing intermediate space between the lower side of the structural component 10 and the upper side of the guide element 30, pushed rearward and held, e.g. by way of projections and grooves, in a form-fit manner between the two resilient components of the prosthetic foot 10.

It is already possible to gather from FIG. 1 that the structural component 10 has an integral embodiment and is designed as a leaf spring, advantageously made of a fiber-reinforced polymer composite, and the arc 16, which has a form that is convexly arched toward the outside, projects beyond the rear end of the guide element 30 in the posterior direction. The spring-damper system 40 is dimensioned in such a way here that the part of the structural component 10 projecting beyond the rear end of the guide element 30 extends above a natural ankle, or in the region thereof, such that the prosthetic foot 1 can be readily inserted into a shoe.

As a result of the spring length that is increased in the posterior direction, it is possible to provide an increased overall spring length with, at the same time, a flat prosthetic foot such that a larger amount of energy can be stored and deeper sinking-in can occur during a heel strike without it being necessary for the material strength of the structural component 10 to be excessively increased, which would necessarily be to the detriment of the durability or adjustability and elasticity during a heel strike.

The guide element 30 is substantially thinner than the structural component 10 in order to ensure easy deformability when the heel strike occurs. As a result, the guide element 30 can easily be swiveled about an axis extending perpendicular to the running direction and extending in the plane of the guide element such that there is only a small energy transfer or low force introduction onto the forefoot region 20 via the guide element 30 in the case of a heel strike. Swiveling about a vertical axis or about an axis oriented along the longitudinal extent of the prosthetic foot 1 is not possible, or only possible to a very restricted extent, due to the structure of the guide element as a leaf spring, and so a supination movement or pronation movement of the guide element 30 is avoided when deflecting or compressing the spring-damper system.

The form-fit element 5, also referred to as heel cap, which is arranged at the rear end of the guide element 30 can form a heel such that there is increased clear space from the floor at the rear end of the guide element 30. This heel can be formed by the sole element 60, which may consist of a compressible, elastic material, so as to bring about a soft introduction of force into the guide element 30 in the case of a heel strike.

The forefoot portion 20 is embodied as a leaf spring and allows deformation under forefoot loading. The guide element 30 is attached to the structural component 10 in the sagittal plane with low moment levels. Here, the sole element 60 is embodied in such a way that, in addition to a compression of the spring-damper system 40, a displacement of the resultant floor reaction force fitting to the load sets in by virtue of loading in the heel region such that the point of force introduction migrates as uniformly as possible along the direction of longitudinal extent of the prosthetic foot 1 during the heel-toe movement. When rolling from the heel to the forefoot, there is a transfer of the energy stored after the initial heel strike in the spring-damper system 40 to the forefoot portion 20 by virtue of not only the forefoot spring being compressed but also the spring-damper system 40 being relaxed, releasing the energy stored therein and thereby reducing a delaying effect as a result of the deformation of the forefoot portion 20 of the forefoot.

An overload stop 70 is provided at the structural component 10, said overload stop 70 restricting the compression travel of the guide element 30, for example in the case of peak loads in extraordinary situations, e.g. in the case of a jump from an elevation or the like. The overload stop 70 is embodied as a projection of the upper form-fit element 6 such that, in the case of excessive load, the overload stop 70 can come into direct contact with the lower form-fit element 5 and prevents further deformation and compression of the spring-damper system 40.

Figure 2:
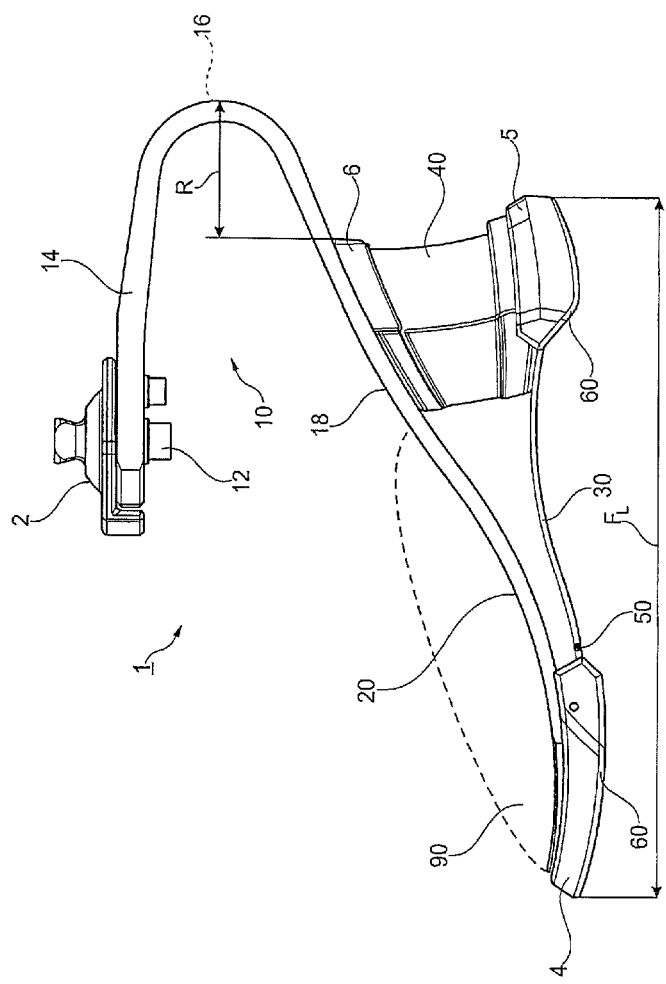
FIG. 2 shows a side view of FIG. 1.

FIG. 2 shows the embodiment in accordance with FIG. 1 in a side view, comprising cushioning 90 which is arranged at the top side in the region of the forefoot portion 20 and which can be fixed reversibly to the top side, for example by way of a hook-and-loop fastener or the like. In the side view, it is possible to identify that the forefoot portion 20 extends up to the tip of the foot region of the prosthetic foot 1 and lies on the top side of the alignment device 4. The side edges of the structural component 10 are at least partly covered by sidewalls which project upwardly from the alignment device 4 such that protection of the sensitive side edges in the case of fiber-reinforced leaf springs is provided just like the protection for surrounding materials from the edges of the leaf spring. Moreover, the cushioning 90 can provide additional protection.

Within the alignment device 4, provision is made of an insertion opening (not depicted here), into which the guide element 30, which is likewise embodied in the form of a leaf spring, is inserted. The guide element 30 projects virtually completely into the alignment device 4; only a small tip region serves as a front termination and for protection against strike loads. The alignment device 4 is preferably made of an elastic material and adhesively bonded in a permanent manner to both the structural component 10 and the guide element 30. To this end, at least one cavity is arranged within the alignment device, said cavity being filled with an adhesive. A front sole element 60 can be arranged or formed at the lower side of the alignment device 4 in order to enable easy rolling over in a manner analogous to the sole element 60 in the case of the heel cap 5.

The heel cap 5 or the form-fit element 5 likewise has a reception slot for the guide element 30, the guide element 30 being inserted into the slot and held either by way of form-fit elements or by way of adhesive bonding or welding within the form-fit element 5.

In the side view, it is possible to identify that the guide element 30 has a form contoured from front to back with a form design that is initially convex, then concave and then convex again. As a result, the overall spring length is increased and a rollover movement is made easier, both during the heel strike and also during the terminal stance phase. The concave region of the guide element 30 is arranged in the midfoot region of the prosthetic foot 1 and models the natural arching of the foot.

Furthermore, it is possible to identify that the upper form-fit element 60 and hence also the upper contact face of the spring-damper system 40 with the connection portion at the lower side of the structural component 10 lie approximately in a plane with the rear end of the guide element 20. The arc 16 extending in the posterior direction beyond the form-fit element 6 and also beyond the posterior end of the guide element 30 has a projection R which is approximately one eighth of the overall foot length FL, i.e. the entire length from the tip of the foot to the posterior end of the heel cap 5. As a result of the backwardly oriented projection R, the effective spring length of the prosthetic foot 1 is massively increased, and so a greater energy storage capability can be achieved with, simultaneously, a greater compression travel and, at the same time, a narrow spring design since the stored energy is effected by way of the increased spring length and not by way of a thickening of the material in the leaf spring of the structural component 10. The thinner the design of a leaf spring made of a fiber composite is, the more durable it is since lower shearing forces occur within the leaf spring.

The contact face of the spring-damper system 40 with the structural component 10 is advantageously effected in the region of the connection portion 18, i.e. in the region in which the convex form of the arc 16 merges into the concave shape of the connection portion 18. The spring-damper system 40 made of a foam material or elastomeric element guides the forces occurring when treading during the initial heel strike directly in the direction of the connection adapter 2 due to the orientation of the spring-damper element in the direction of the connection adapter 2. Due to the introduction of the forces into the connection region, there is a compression during the heel strike over the proximally adjoining portion of the structural component 10, i.e. in the arc 16 and the connection portion 14, and so there is no force transmission and energy storage in the forefoot portion 20. That is to say, the forefoot portion 20 is not negatively charged during a heel strike since there is no introduction of force into the forefoot portion 20. Due to the low material strength of the guide element 30 and the simplified bending about a notional swivel axis 50 perpendicular to the plane of the sheet, there will also be no energy influx into the forefoot portion 20 by way of the guide element 30. When forming the spring-damper system 40 from a foam or corresponding elastomeric element, there are no shearing forces within the spring-damper element, and so no tensile forces are introduced into the guide element 30 either.

The spring-damper element 40, which may have an interchangeable design, advantageously has a progressive spring-damper behavior and can e.g. have a two-component foam, a two-component elastomer or a combination of a plurality of materials and/or a plurality of densities of the same materials in order to ensure the desired spring-damper properties. The spring-damper element 40 is held in a form-fit manner in the form-fit elements 5, 6; undercuts are provided in the form-fit elements 5, 6 which engage in recesses or grooves in the spring-damper system 40.

In the side view of FIG. 2, it is furthermore possible to identify that the structural component 10 is embodied as a single-piece leaf spring as a hinge-free prosthetic foot 1 and has a spring extension in the region of the ankle in order to increase the effective spring length. A vertical displacement of the prosthetic foot 1 is more easily possible as a result of the increased effective spring length, with the vertex of the arc 16 projecting beyond the natural overall foot length FL, i.e. beyond the rear end of the guide element 30 embodied as a base spring. The prosthetic foot 1 is immediately insertable into a shoe and does not require a cosmetic foot covering. On account of the design thereof, the prosthetic foot 1 has a high deformation capability, a large energy storage capacity during the stance phase, provides high durability due to the comparatively low material strength of the leaf spring component and enables a low prosthetic foot height. Moreover, the embodiment provides a heel component, and so it is possible to wear the prosthetic foot 1 during normal activities as well. Moreover, the prosthetic foot 1 is preferably suitable for sports activities such as jogging or the like. Sports feet known from the prior art can generally not be worn in a shoe and are generally not suitable for standing. Although conventional hinge-free prosthetic feet for daily use can be inserted into a cosmetic foot covering or possibly even directly into a shoe, they do not permit the high level of deformability afforded by the prosthetic foot 1 of the present invention.

In the side view in accordance with FIG. 2, the initially substantially horizontal leaf spring can be identified on the connection means 2 in the region of the connection portion 14, from which a slightly downwardly tilted course extends in the rearward, posterior direction. In principle, it is also possible for a further horizontal course or a slightly upwardly inclined course to join thereon. The connection portion 14 is adjoined by the rear arc 16, which is situated over approximately one eighth of the overall foot length FL behind the end of the heel of the prosthetic foot 1 and has concave curvature. At the end of the concave curvature, the structural component 10 merges into convex curvature with a larger radius compared to the arc 16 and from there it merges again into concave curvature with likewise a larger radius of curvature than the arc 16. During the heel strike, the spring-damper system 40 and the spring portion with the arc 16 and the connection portion 14 are connected in series, a deformation of the structural component 10 in the form of a displacement of the connection means 2 in the direction of the floor is possible as a result of the rear arc 16. To this end, the arc 16 projects over the line of the force which extends rearward from the heel strike to the connection means 2 through the spring-damper system. The greater the rearward projection R is, the softer the prosthetic foot 1 becomes; the maximum projection R emerges from the intended use, the employed materials and the preferences of the prosthetic foot user.

When rolling over to the mid-stance phase, the spring-damper system 40 is partly relieved since it is now only the forefoot portion 20 and the front sole element 60 which contact the floor. As a result, the whole structural component 10 begins to deform. The previously still non-deformed forefoot portion 20 is bent, the vertical force introduced during the mid-stance phase is converted into potential energy by a further deformation in the region of the arc 16 and of the connection portion 14. As a result, the vertical strike load is reduced. In the case of further rolling over to the forefoot, the spring-damper system 40 is relieved completely and the structural component 10 carries the entire load. Due to the arc 16, this is initially primarily vertically instead of in the return when lifting the forefoot and turns in the direction of the running direction during the last third of unloading. The vertex of the arc lies approximately in the region of the natural ankle and is displaced over the natural ankle position in the posterior direction. The heel stiffness is primarily controlled by the spring-damper system, the arc 16 and the connection portion 14 of the structural component 10. The point of attack of the force is held close to the heel for as long as possible due to the shaping of the sole element 60 in order to design the deformation property of the heel to be comfortable for the user. As a result of the narrow embodiment of the guide element 30, little force is applied to the forefoot portion 20; the latter is reduced further by the twice curved shape of the heel element.

Figure 3:
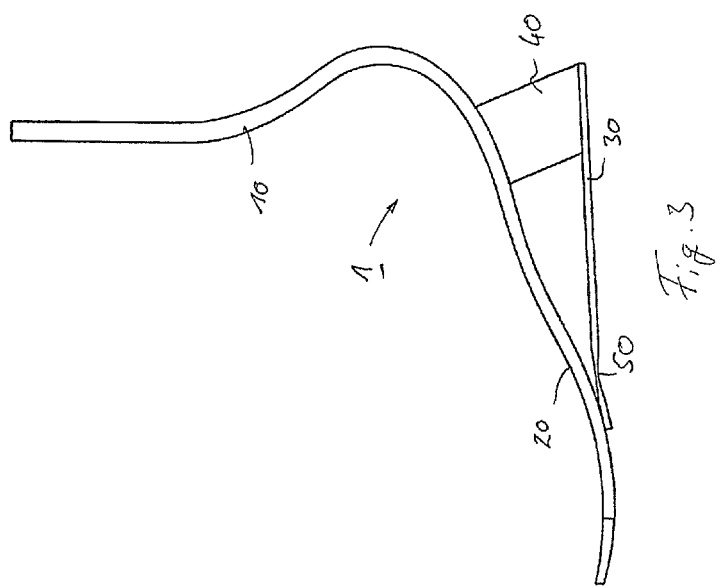
FIG. 3 shows a variant with a modified structural component.

FIG. 3 shows a further variant of the prosthetic foot 1. In the depicted exemplary embodiment, the prosthetic foot 1 is equipped with an integral combination of the support structure 10 and the forefoot element 20. Then, there is fastening to a below knee shank or other fastening elements at the proximal end of the support structure 10. The plate-like, substantially planar guide element 30 is fastened, e.g. laminated, welded, screwed or adhesively bonded, to the floor-facing lower side in the ball region of the forefoot element 20. The axis 50, which is embodied as a swivel axis, is formed by a film hinge which allows swiveling about an axis lying within the film hinge; however, a rotation about a longitudinal axis in the anterior-posterior direction and about an axis in the proximal-distal direction is largely prevented due to the stiffness of the guide element 30. The spring-damper system is fastened immediately on the support structure 10 in the vicinity of the ankle.

Figure 4:
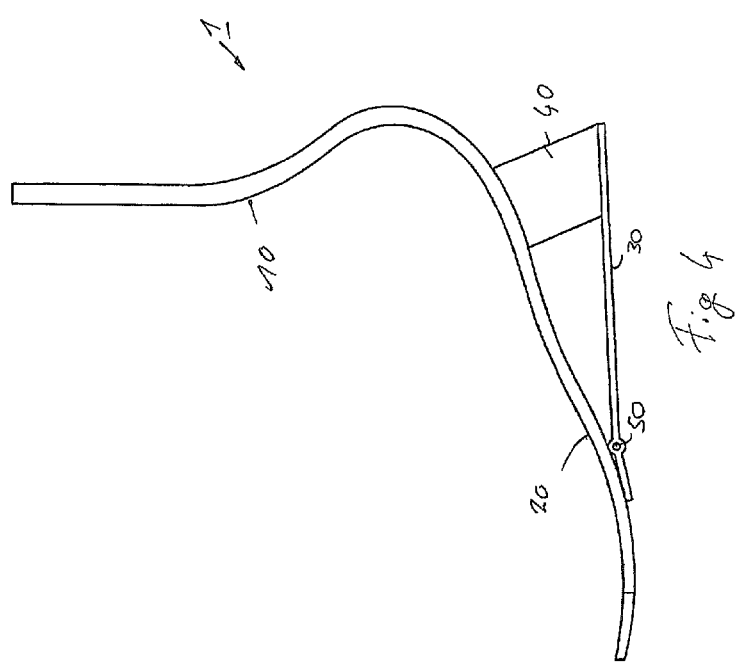
FIG. 4 shows a variant of FIG. 3.

A variant of FIG. 3 is depicted in FIG. 4, in which a free hinge with an axis 50, which hinge can be embodied as a flap, is provided instead of a film hinge.

What is common to all embodiments is that a heel-side spring-damper system 40 is connected in the sagittal plane to further elements of the foot structure, i.e. either to the forefoot portion 20 or the structural component 10, with low moment levels by way of the guide element 30. Forces away from the effective direction of the spring-damper element 40 are taken up in the guide element 30 and dissipated by way of the hinge which permits swiveling about the axis 50. On the upper side thereof, the spring-damper system 40 is supported near the ankle at the structural component 10, the guide elements 30 being substantially embodied as planar structures and supporting the spring-damper system 40, which is supported at the lower side of the structural component, on the lower side. In the case of an eccentric force introduction into the heel, the planar structure of the guide element 30 can however twist such that the contact surface is enlarged. The horizontal forces, which are introduced when the heel is loaded and which act in the running direction or perpendicular to the running direction, are taken up by the structure of the guide element 30 and introduced into the support structure near the ankle by way of the hinge which is embodied as a swivel axis 50. Hence, the articulated fastening of the guide element 30 supports the heel-side spring-damper system against shearing in the case of horizontal forces. Here, the articulated mount is embodied in such a way that, as a result of the width thereof, it is well suited to take up the occurring shearing forces. It is also possible for a plurality of bearing points to be arranged next to one another on a common axis 50 in order to realize a successive arrangement of hinges.

Prosthetic feet are intended to soften the force during the treading strike, impart sufficient stability when rolling over and return that amount of energy during pushoff which the user can easily control when walking. The deformation of the individual components required to this end tests the capability of the employed high performance materials to their limits. Therefore, spring systems with elements which are connected to one another in a virtually rigid manner are often used in prosthetic feet made out of high performance materials. These elements protect one another from overload by the coupled effect but, on the other hand, do not allow independent effect on a different load introduction, e.g. from heel and forefoot.

Figure 5:
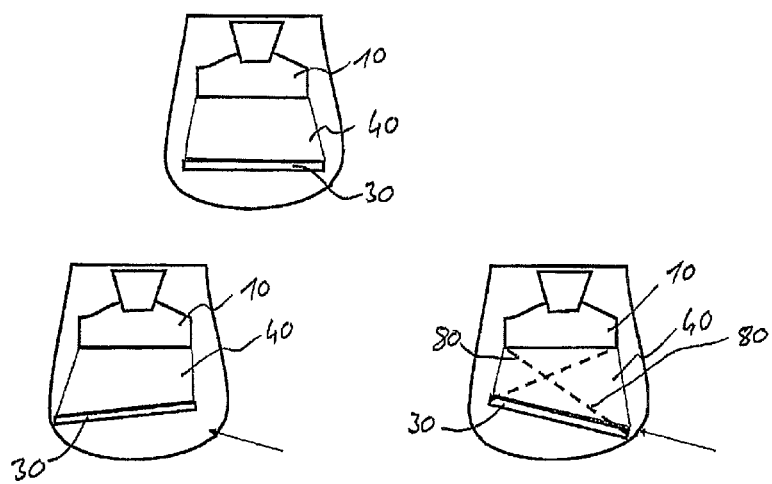
FIG. 5 shows a schematic illustration of a lateral-force compensation.

FIG. 5 shows, in a rear view, the structural component 10 and the spring-damper element 40, and also the guide element 30. Depicted in the upper illustration is an unloaded prosthetic foot; it is possible to identify that the guide element 30 is coupled to the structural component 10 by way of the heel-side spring-damper system 40. A force transfer from the guide element 30 to the structural component 10 should only take place within the effective direction of the spring-damper system 40; in the case of a heel strike, this is the direction of the force within the sagittal plane and from distal to proximal within the medial plane. Forces outside of the effective direction of the spring-damper system 40 are taken up by way of the guide element 30 and dissipated by virtue of the virtually articulated mount, either into the forefoot portion 20 and, via the latter, into the structural component 10 or directly into the structural component 10. The sole-side structure of the guide element 30 for guiding the spring-damper system 40 is embodied distally in such a way that, as a result of loading the heel and in addition to a compression of the spring-damper system 40, a displacement of the resultant floor reaction force, which fits to the loading, sets in, for example as a result of the torsion of the guide element 30. Such a situation is shown in the left-hand lower illustration of FIG. 5. A lateral force acts on the guide element 30, leading to displacement of said guide element 30.

In the right-hand lower illustration of FIG. 5, provision is made of an exemplary embodiment with two stabilizing elements 80 in the form of tension elements which are arranged in a crossing manner. Here, the guide element 30 is mounted and supported by the stabilizing elements 80 in such a way that a lateral force is not only supported but that the laterally attacking force is counteracted on the side of the force effect by a swivel movement by way of a displacement of the point of attack of the force.

Figure 6:
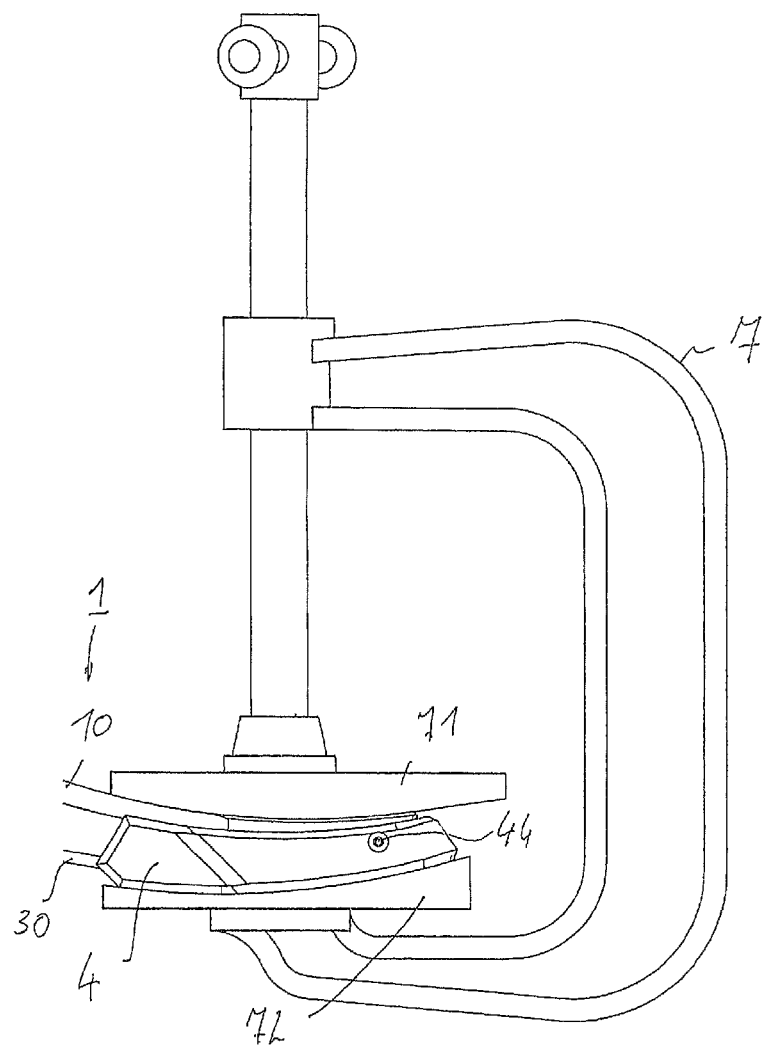
FIG. 6 shows a side view of an orthopedic component during manufacturing.

In a side view, FIG. 6 shows a schematic illustration of a front part of a prosthetic foot 1. The prosthetic foot 1 has two structural components 10, 30 which are produced as leaf springs from a fiber-reinforced plastic. The forefoot region of the prosthetic foot 1 is depicted; the first structural component 10 is a forefoot spring, the second structural component 30 is the guide element. The forefoot spring 10 extends obliquely upward to an upper connection point, at which fastening devices or connection means for fastening to a below knee tube or a below knee shank are able to be fastened. The guide element 30, which is also referred to as a base spring, leads into the heel region, wherein a heel spring can extend from the base spring 30 to the forefoot spring 10 and/or to the upper connection means.

The structural component 10 and the guide element 30 are assigned to an alignment device 4 which is embodied as a plastic molded part. The alignment device 4 can consist of a polyurethane, a technical polyethylene, a technical polyurethane, rubber or any other plastic, preferably an elastomer. The alignment device 4 has an insertion slot for the guide element 30 and a reception region at the upper side for the first structural component 10, onto which the first structural component 10 can be supported. The support region is framed by walls such that the first structural component 10 can be supported with a defined position in relation to the alignment device 4 when the contour of the structural component 10 rests against the walls around the support region.

The guide element 30 is inserted into a slot (not depicted here) within the alignment device such that the lower side of the guide element 30 or of the leaf spring is covered by a closed surface of the lower side of the alignment device 4. A spacer is formed between the structural component 10 and the guide element 30, said spacer holding the two components securely at a distance from one another. As a result of inserting the guide element 30 into the alignment device 4, said former component is also assigned in a defined manner, for example by virtue of being guided in a slot or in a groove within the receiving device 4. As a result, the two components 10, 30 and the receiving device 4 form a cavity which is substantially closed-off. A feed connection 44 is provided in a side wall of the alignment device 4, said feed connection having a fluidic connection with the cavity (not depicted here), through which it is possible to insert or pump adhesive into the cavity. On the side distant from the feed connection 44, provision is made of an outlet channel, which likewise has a fluidic connection to the cavity, such that the air situated within the cavity can emerge and the cavity can be completely filled with adhesive.

The components 10, 30 and the alignment device 4 are held in a press 7, which can be formed as a conventional vice. Two press shoes 71, 72 are arranged on the press 7 and have a contour corresponding to the respectively assigned contour of the orthopedic component 1. In the illustrated exemplary embodiment the upper press shoe 71 is provided with a convex curvature and the lower press shoe 72 is provided with a concave curvature so that on the one hand the lower side of the receiving device 4 and on the other hand the upper side of the first structural component 10 can bear over the entire surface against the surface of the relevant press shoe 71, 72. If the press 7 is closed and pressure is exerted onto the press shoes 71, 72, the first structural component 10 will be pressed against the surface of the support face on the alignment device 4 so that the cavity formed between the structural component 10 and the guide element 30 above and below and at the side faces by means of the alignment device 4 is closed and adhesive can be fed only through the feed connection 44, and air and any excess adhesive can escape through the outlet channel.

Following the introduction of the adhesive, the pressing force is maintained until the adhesive has cured, so that a permanent connection between the first structural component 10, the guide element 30, and the alignment device 4 is obtained. After curing of the adhesive, the alignment device 4 remains on the orthopedic component 1 and serves in turn as protection for the structural component 10 and the guide element 30 and, secondly, as functional component of the orthopedic component, for example as a shaping for the prosthetic foot, as a cushion, as a sole structure, or in other embodiments as a receiving device or protective device for further components.

Figure 7:
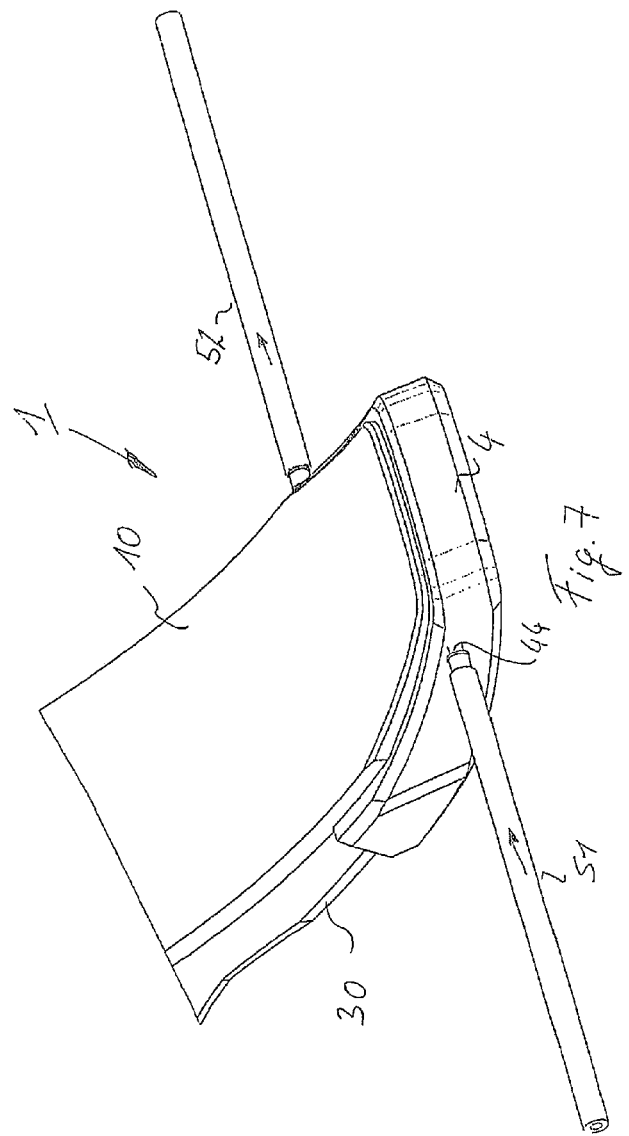
FIG. 7 shows a perspective view with feed and outlet devices.

FIG. 7 shows, in a perspective oblique plan view, the manufacture of the orthopedic component 1, or at least the connection of the structural component 10 and the guide element 30 to the alignment device 4. A feed device 51 is attached to the alignment device 4 at the feed connection 44, which feed device in the illustrated exemplary embodiment is formed as a tube or pipe and through which adhesive is introduced into the cavity (not illustrated) as indicated by the arrow. The cavity is formed and closed on the upper side and on the lower side by the structural component 10 and the guide element 30, on the front side and on the side edges by the side walls of the alignment device 4, and on the rear side between the leaf springs 10, 30 by a spacer, which bears tightly both against the lower side of the first structural component 10 and against the upper side of the guide element 30. The press 7 is not illustrated in FIG. 7; however, the assignment of the respective components 4, 10, 30 by the press 7 or another suitable fixing device is maintained during the feed of the adhesive.

Adhesive is introduced into the cavity through the feed device 51 and the feed connection 44, and the air disposed in the cavity is displaced by the adhesive and is transported away by an outlet device 52. The outlet device 52 is connected at an outlet channel (not illustrated), which is fluidically connected to the cavity within the receiving device 4, so that air and any excess adhesive can escape from the outlet channel through the outlet opening 51, as indicated by the arrow. Both the feed connection 44 and the outlet channel are preferably arranged in a spacer, which ensures that the leaf springs 10, 30 are held at a distance from one another. It is thus ensured that, by the arrangement of the leaf springs 10, 30 on or in the alignment device 4, are not blocked in relation to one another by the assignment of the leaf springs 10, 30.

The press 7 (not illustrated) holds the assignment of the components 4, 10, 20 in relation to one another until the adhesive has cured. Once the adhesive has cured, the feed device 51 and the outlet device 52 are separated from the alignment device 4, for example snapped off, so that a practically smooth termination of the alignment device 4 in the region of the feed connection 44 and the outlet channel can be achieved. This can be ensured for example by a predetermined breaking point on the feed device 51 and/or the outlet device 52 in the region of the connection to the alignment device 4.

Figure 8:
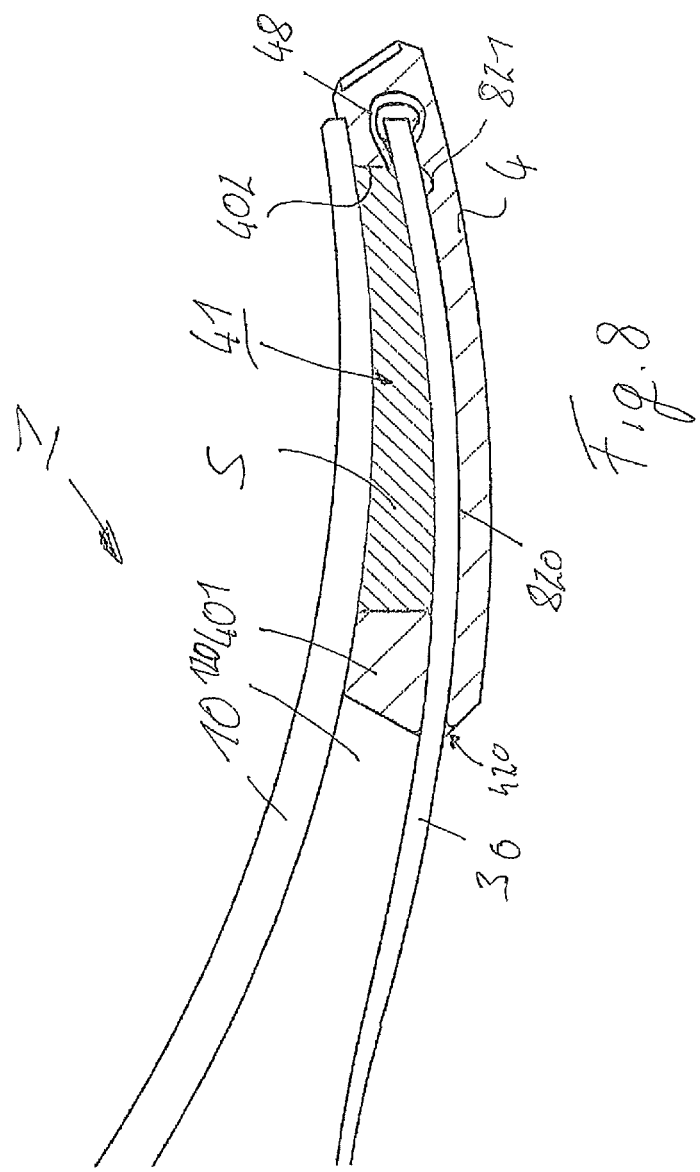
FIG. 8 shows a sectional view of part of an orthopedic component.

FIG. 8 shows a sectional illustration through the front part of a finished, assembled prosthetic foot 1 with an upper first structural component 10 resting on the alignment device 4, said structural component 10 being in the form of a forefoot spring made of a fiber-reinforced plastics material, with the alignment device 4, and with the guide element 30 inserted into the alignment device 4, said guide element being in the form of a base spring, which is likewise formed as a leaf spring made of a fiber-reinforced plastics material. The upper leaf spring rests on an upper support face, and the lower leaf spring rests on a lower support face 820. A channel 48 is formed at the front end (on the right-hand side in the illustrated exemplary embodiment) of the alignment device 4 and leads from the lower side of the guide element 30 to the cavity 41, which is enclosed by the guide element 30, the first structural component 10, and the alignment device 4. Indentations 821 are formed in the support face 820, which is formed by the surface of the base of the alignment device 4 facing toward the guide element 30, so that adhesive 5 completely filling the cavity 41 can infiltrate the indentations 821 also below the guide element 30 on account of a structured surface or the indentations 821, which are fluidically connected to the cavity 41, such that at least the lower guide element 30 is surrounded by a number of sides or at a number of points by the adhesive 5. A feed connection 44 is advantageously arranged at the geodetically lowest point of the alignment device 4 during the assembly, for example on the lower side of the alignment device 4 in the case of the presented orientation, and is fluidically connected both to the indentations 821 and, on account of the channel 48, also to the cavity 41. If adhesive 5 is now fed at the lowest point, said adhesive pushes through the structured surface on the upper side of the base of the alignment device 4 through the indentations 821, through the channel 48 into the cavity 41, wherein the air previously enclosed therein is guided away through the outlet channel (not illustrated).

FIG. 8 additionally shows an insertion opening 420 for the guide element 30, which opening in the illustrated exemplary embodiment is formed as a slot and ends at the height of the upper side of the base forming the support face 820. A first spacer 490 is arranged above the insertion opening 420, on which spacer the first structural component 10 is rested so that an intermediate space 120 is formed between the first structural component 10 and the guide element 30, which intermediate space continues also toward the front, since a second spacer 402 is formed at the front end and serves as a support face for the first structural component 10. It can be seen from FIG. 8 that the insertion opening 420 is dimensioned so that the lower leaf spring can be pushed through and inserted in a tightly bearing manner. As the adhesive 5 is introduced, adhesive is thus prevented from being able to escape from a region of the insertion opening 420 around the guide element 30. The sealing effect is increased by the pressing of the first structural component 10 against the spacer 401 and therefore against the guide element 30. On account of the second press shoe 72, the support face 820 bears tightly against the guide element 30 so that no adhesive can escape as the cavity 51 is filled.

The front end of the guide element 30 is received completely in the receiving device 4 and is protected and surrounded on all sides: the edging or framing of the upper support face for the first structural component protects the leaf springs at the periphery; the protection on the lower side is provided by the adhesive and the support face on the alignment device 4; merely the upper side is unprotected.

Figure 9:
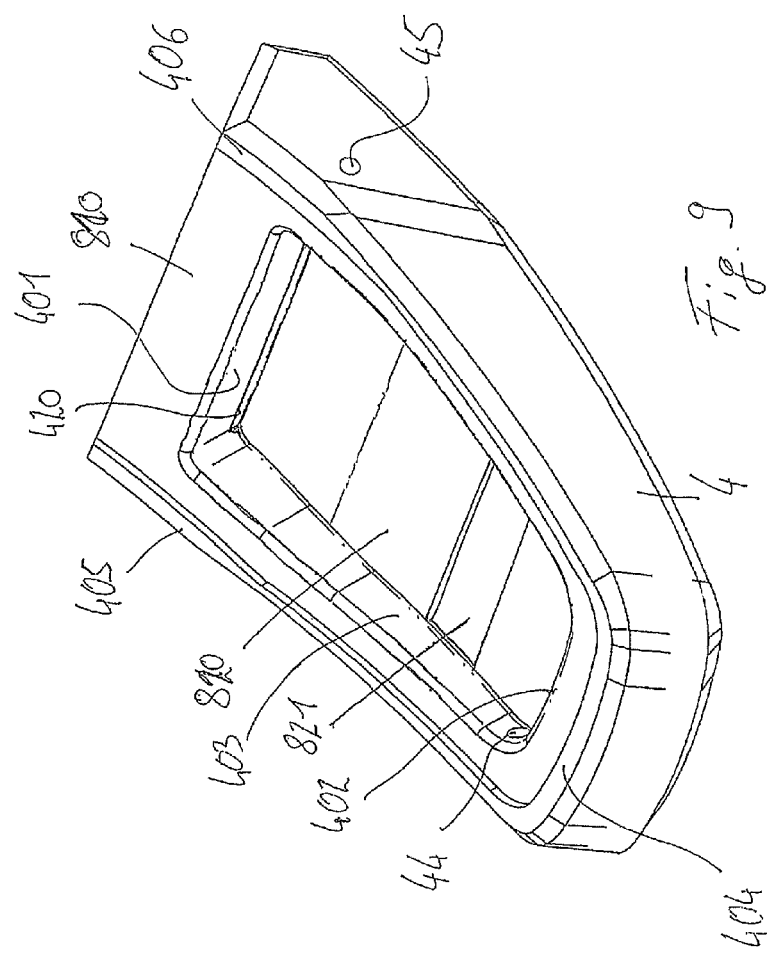
FIG. 9 shows a perspective view of an alignment device.

FIG. 9, in a perspective illustration, shows a receiving device 4 in accordance with the embodiment of the previous drawings. Besides the feed connection 44, the outlet channel 45, and the lower support face 820, the indentation 821 is illustrated slightly enlarged. The channel 48, which is fluidically connected to the indentation 821, is not illustrated. The spacers 401, 402 on the rear side and the front side can be seen. The spacers 401, 402 at the same time form, on their upper sides, an upper support face 810 for the first structural component (not illustrated), which is pressed by its lower side against the support face 810. The insertion slot or the insertion opening 420 ends at the height of the lower support face 820. A groove is made in the lateral spacers 403 laterally next to the support face 820, into which groove the leaf-shaped guide element 30 is inserted until it contacts the front termination of the alignment device 4.

The upper support face 810 is edged by side walls 404, 405, 406, which can correspond in terms of their material thickness to that of the upper structural component 10. Due to the side walls 404, 405, 406, a defined assignment of the upper structural component 10 to the alignment device 4 and therefore to the lower guide element 30 is ensured when the front and lateral edges of the structural component 10 bear against the respective side walls 404, 405, 406. If the height of the side walls 404, 405, 406 corresponds to the material thickness of the upper structural component 10, the surfaces can terminate in a flush manner.

Figure 10:
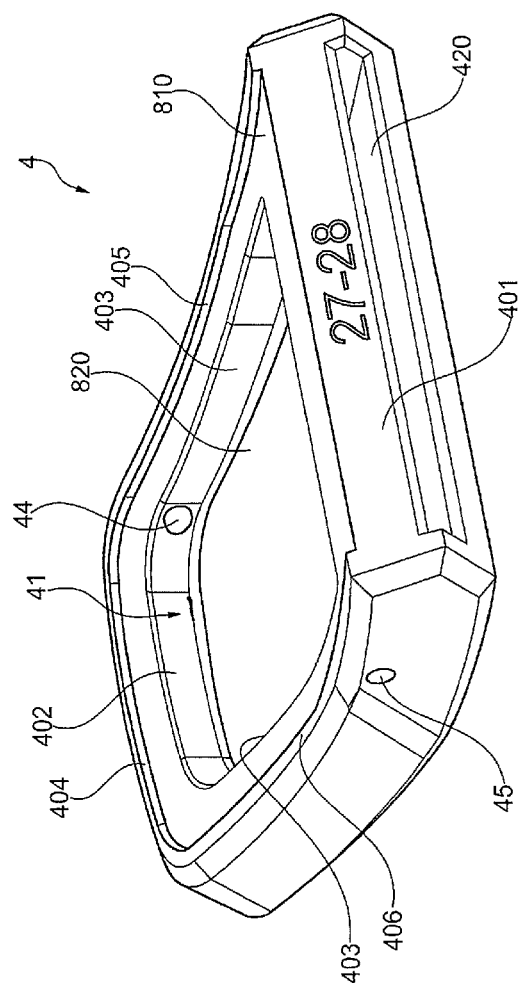
FIG. 10 shows another view of the alignment device of FIG. 9.

FIG. 10 shows the alignment device 4 in accordance with the previous embodiments in an oblique view from behind, from which the rear spacer 401, the front spacer 402, and the insertion opening 420 are very clearly visible. It can also be seen that the feed connection 44 is lower than the outlet channel 45, wherein both the feed connection 44 and the outlet channel 45 are formed within the spacer 403. A groove, in which the guide element 30 can be inserted, is formed by an undercut in side walls formed below the spacers 403. The elevated side walls 404, 405, 406, which protrude past the upper support face 810, can also be seen, as can the support face 820 on the upper side of the base of the alignment device 4, which support face is flat in the illustrated exemplary embodiment. A receptacle is formed within the alignment device 4 by the side walls 402, 403 and the rear spacer 401, which receptacle can be completely filled with adhesive. By inserting the lower guide element 30 through the insertion opening 420, the insertion opening 420 is closed, so that the receptacle is only open upwardly after the insertion of the guide element 30. If the structural component 10 (not illustrated) is rested on the upper support face 810, the cavity 41 is closed. Once the cavity 41 has been filled with the adhesive, this is connected in an adhesively bonded manner both to the alignment device 4 and to the two leaf springs 10, 30.

Figure 11:
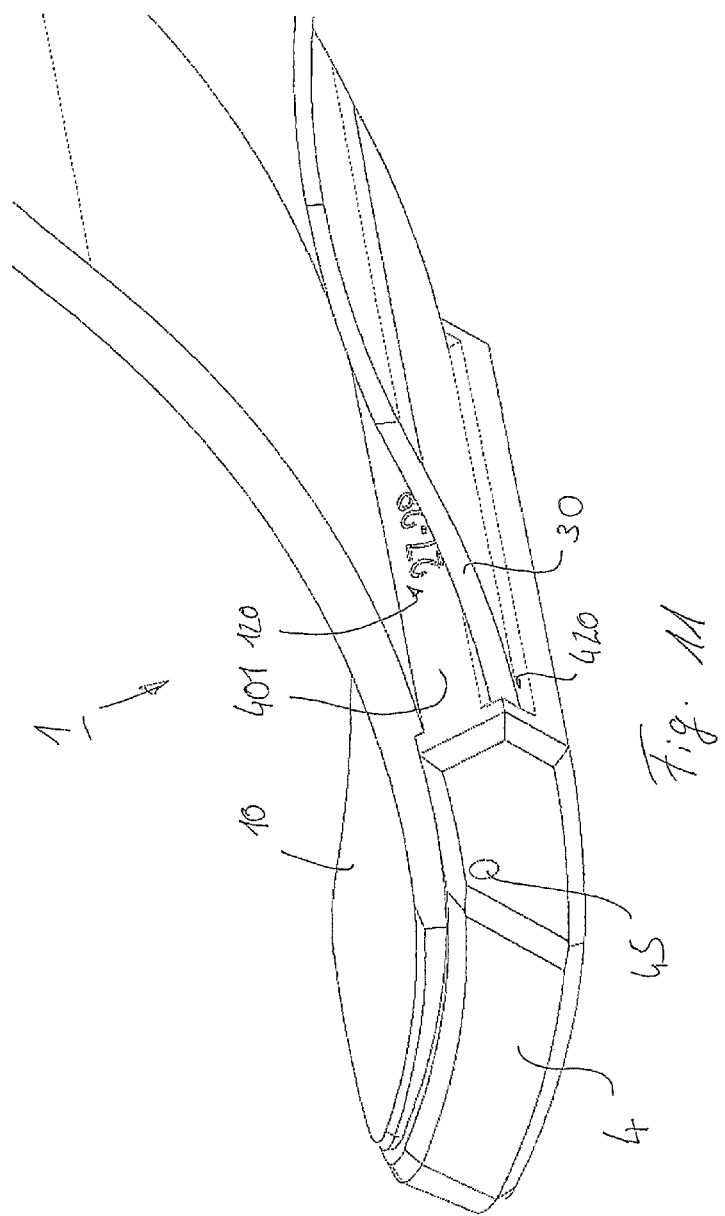
FIG. 11 shows a partial illustration of an orthopedic component from obliquely behind.

FIG. 11 shows a front part of the orthopedic component in the form of a prosthetic foot 1 obliquely from behind in a finished, assembled state. The guide element 30 is inserted into the insertion opening 420, and the upper structural component 10 is rested and held on the support face 810 (not illustrated), with an intermediate space 12 thus being formed, this being ensured by the spacer 401. The outlet channel is arranged in a side wall, and the components 4, 10, 30 are permanently connected via the adhesive within the receiving device 4.

Figure 12:
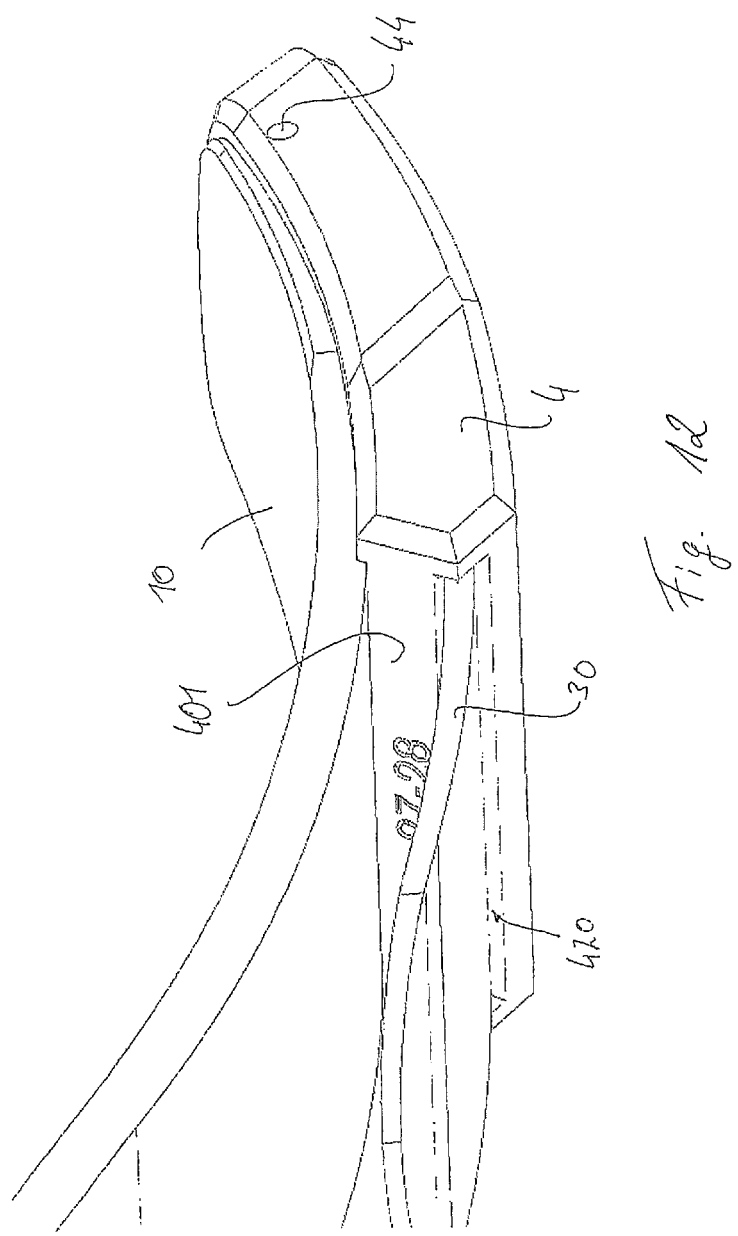
FIG. 12 shows a variant of FIG. 11.

FIG. 12 shows the embodiment according to FIG. 11 from the other side; the feed connection 44 is arranged on a front side wall of the alignment device 4.

Figure 13:
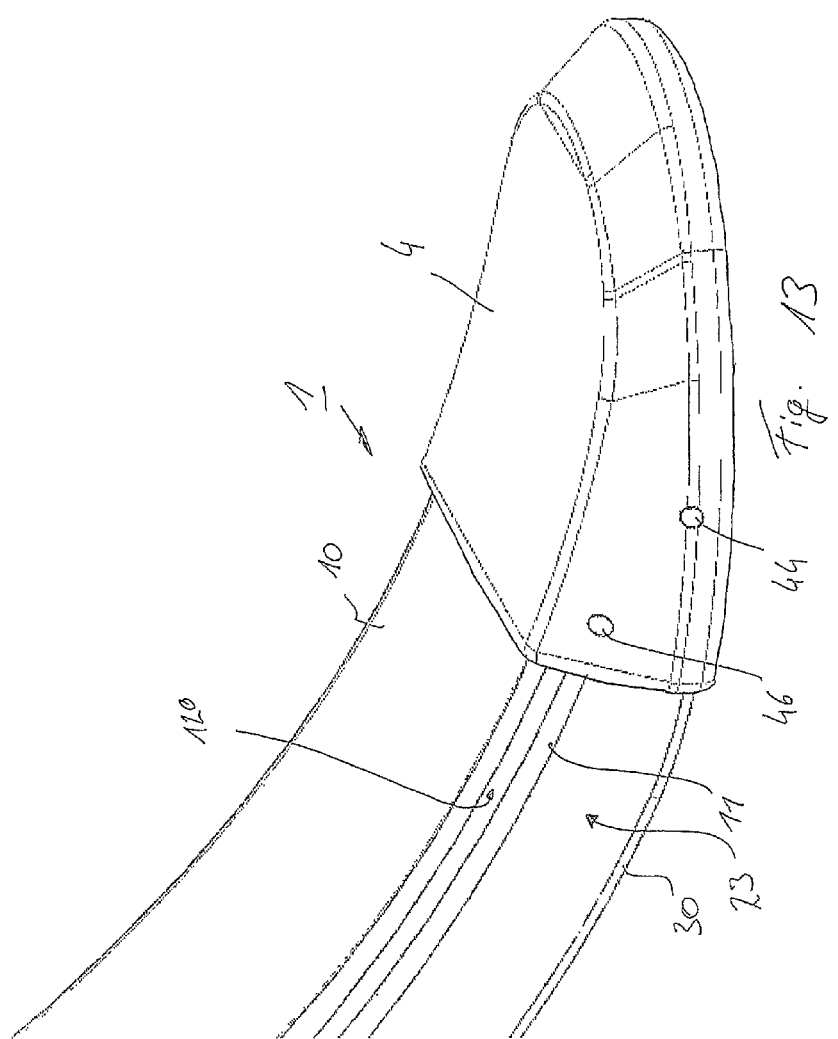
FIG. 13 shows a perspective partial illustration of a second embodiment.

FIG. 13 shows a variant of the invention in which, instead of just two structural components, as is illustrated in FIGS. 6 to 12, three structural components 10, 11, 30 are connected to one another via an alignment device 4. The orthopedic component 1 is again formed as a prosthetic foot and has a base spring as guide element 30. The forefoot spring is formed as a double leaf spring arrangement connected in parallel, comprising two leaf springs as middle structural component 11 and upper structural component 10. The orientation of the double spring and the base spring corresponds to the orientation as has been described further above; however, different orientations and alignments of the components 10, 11, 30 in relation to one another are, in principle, possible and provided.

An intermediate space 23 is formed between the lower guide element 30 and the second, middle structural component 11, whereas a second intermediate space 120 is formed between the first, upper structural component 10 and the middle structural component 11. The intermediate space is formed by corresponding spacers within the alignment device 4.

The alignment device 4, in contrast to the previous embodiment, is closed upwardly, that is to say the upper structural component 10 is not rested on an upper support face in order to close off a cavity, but rather all structural components and the guide element 30 are inserted into the alignment device 4 from the rear side through insertion openings.

Since the spacing of the respective structural components 10, 11 and of the guide element 30 continues within the alignment device 4, at least two cavities are formed within the alignment device 4 and are separated from one another so that, in the illustrated exemplary embodiment, two feed connections 44, 46 are provided, such that the cavities can be filled separately. It is thus possible to provide for example different adhesives, different adhesive temperatures, or other process features when required by the process.

Figure 14:
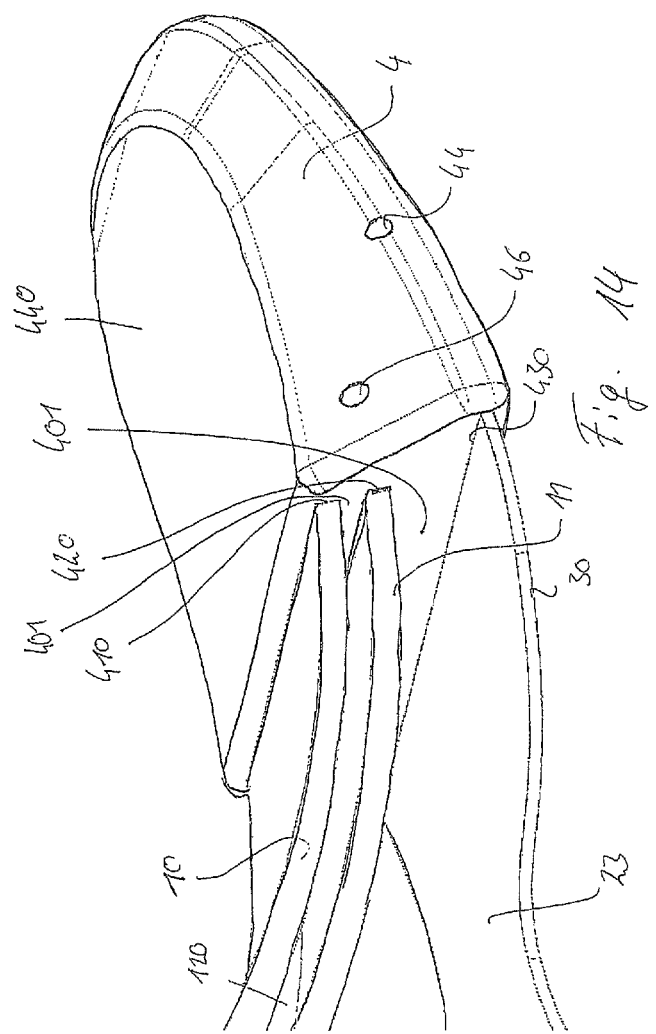
FIG. 14 shows another view of the embodiment of FIG. 13.

FIG. 14 shows the embodiment according to FIG. 13 in an oblique view from behind. The three insertion openings 410, 420, 430 on the rear end face of the alignment device 4 can be seen, as well as the two feed connections 44, 46 and the rear spacers 401 formed by the rear wall between the leaf springs 10, 11, 30.

The insertion opening 430 for the guide element 30 is arranged, as in the previous embodiment, at the level of the lower support face 820, and the groove, preferably a peripheral groove in the side wall, and an optionally provided structuring of the support face can also be provided. Instead of the upwardly open design, a cover 440 is provided in the illustrated exemplary embodiment according to FIG. 14 so that the upper side of the upper structural component 10 is also covered by the material of the alignment device 4. The front ends of the structural components 10, 20 and of the guide element 30 are thus surrounded completely by the alignment device 4 and are connected to one another and to the alignment device 4 via the adhesive.

Figure 15:
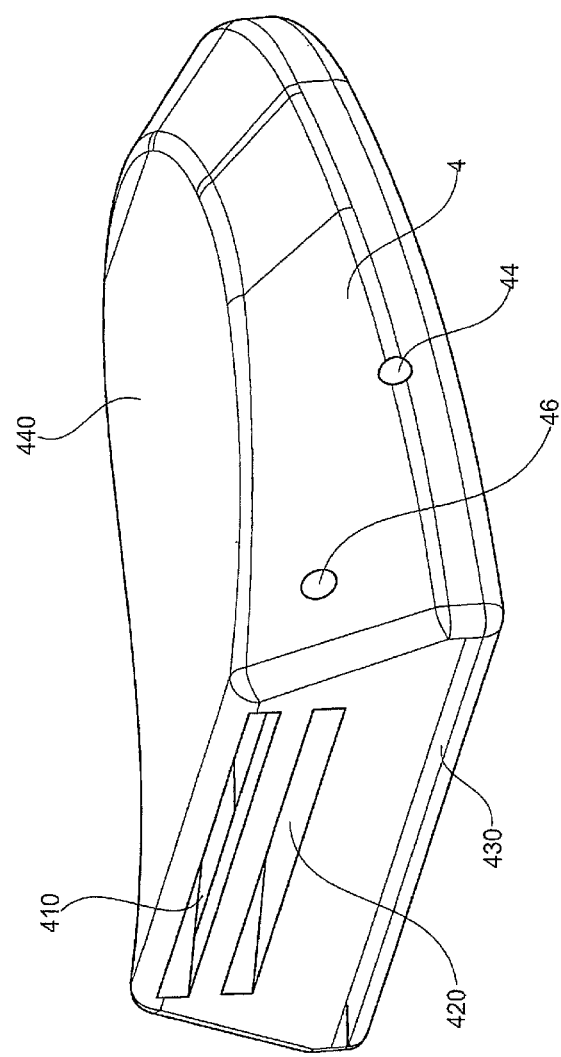
FIG. 15 shows an overall view of an alignment device of the second embodiment.

FIG. 15 shows the alignment device 4 in accordance with the second exemplary embodiment in an isolated illustration. The three insertion openings 410, 420, 430 on the rear side can be seen, as well as the two lateral feed connections 44, 46, which identify access to the intermediate spaces or cavities within the alignment device 4 created by the insertion of the leaf springs 10, 11, 30. The upper cover 440 forms the upper termination, and the base of the alignment device 4 forms the lower termination and a sort of sole in an embodiment of the orthopedic component as a prosthetic foot.

Figure 16:
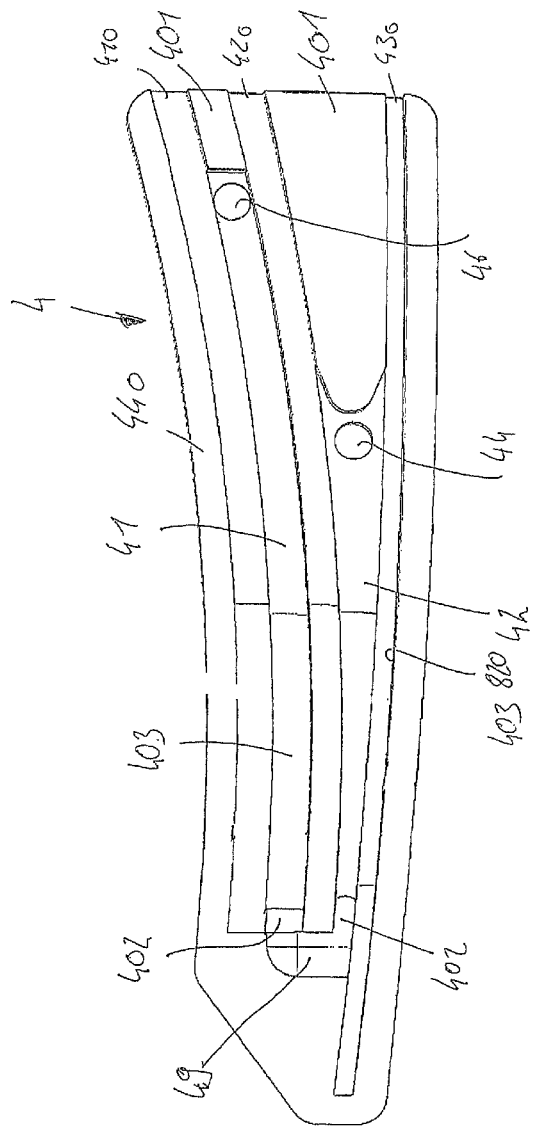
FIG. 16 shows a sectional illustration of FIG. 15.

FIG. 16 shows a sectional view of the alignment device 4, from which the insertion openings 410, 420, 430, the rear spacers 401, and the front and lateral spacers 402, 403 can be seen. A channel passing through the front spacers 402 is also formed so that adhesive are admitted, when it are formed by the side through the feed connections 44, 46 into the cavities 41, 42 by the alignment device 4 and the structural components received therein. As an alternative to the embodiment illustrated in FIGS. 13 to 15, it is possible for just the lower opening 44 to be formed as a feed connection, whereas the upper opening is formed as an outlet channel, such that adhesive passes through the feed connection 44, through the cavity 42 and the channel 49, into the cavity 41 and then exits through the outlet channel. The support face 820 can be structured and can also be washed over or wetted by adhesive so that the middle structural component is surrounded both on the lower side and on the upper side by adhesive and is connected thereon on both sides to a different leaf spring. The closed cover 440 can also be seen, as can the closed front tip, and an insertion groove for the lower structural component, which protrudes beyond the channel 49 in the front direction. The feed connections 44, 46 or the feed connection 44 and the outlet channel are formed in the lateral spacers 403.

Figure 17:
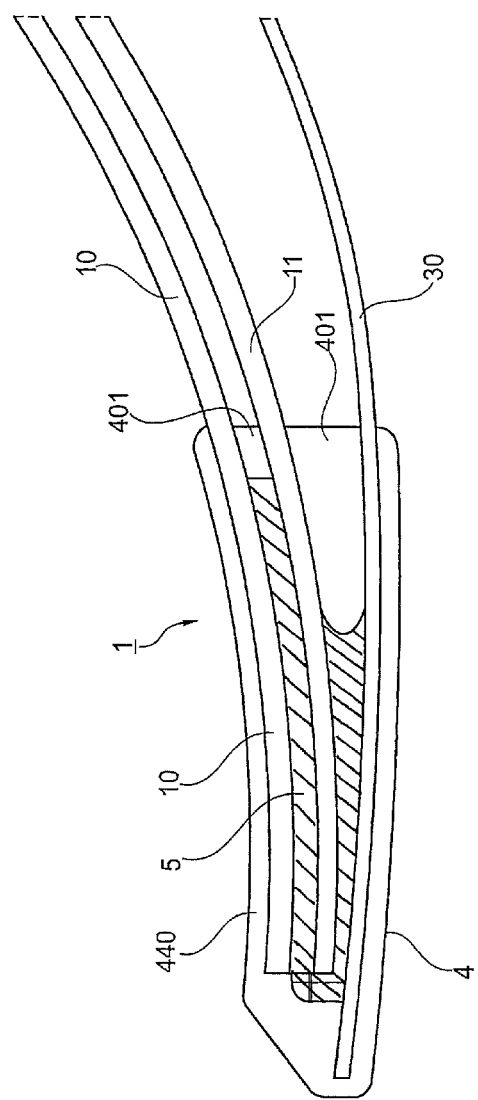
FIG. 17 shows a sectional illustration of FIG. 14.

FIG. 17 shows the front end of the orthopedic component 1 in the assembled state in a schematic sectional illustration. The two structural components 10, 11 and the guide element 30 in the form of leaf springs are inserted through the respective insertion openings into the alignment device 4, and the rear spacers 401, the spacers 403 (not illustrated) and the front spacers 402 are held at a distance from one another in the alignment device 4. The adhesive 5 has been introduced into the cavity 41 through the feed connection 44 (not illustrated), has penetrated through the channel 49 into the upper cavity 42, and has been guided away through the upper outlet channel 45 (not illustrated). No adhesive 5 has escaped rearward during manufacture through the sealing termination of the insertion openings 410, 420, 430 around the leaf springs 10, 11, 30. The adhesive surrounds the second structural component 11 on the upper side, on the front side, and on the lower side.

Figure 18:
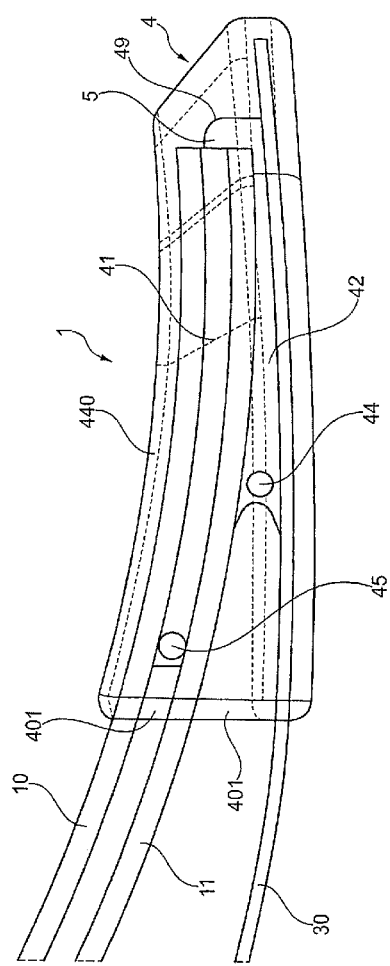
FIG. 18 shows a different view of FIG. 17.

FIG. 18 shows a side view of the assembled prosthetic foot or the orthopedic component 1, in which case, instead of two feed connections, a lower feed connection 44 and an upper outlet channel 45 are provided in the alignment device 4. The three inserted structural components 10, 11, 30 can also be seen, as can the rear spacers 401, the intermediate spaces or cavities 41, 42, which are sealed to the rear by the inserted structural components 10, 20, 30 and the upper cover 440, by means of which the upper leaf spring or the upper structural component 10 is also covered and protected completely by the alignment device 4.

The adhesive is pushed through the feed connection 44 into the lower cavity 42, through the channel 49 into the upper cavity 41, and out through the outlet channel 45; as soon as adhesive exits from the upwardly placed outlet channel 45, the feed of the adhesive through the feed connection 44 is stopped, the components 10, 11, 30 are held in the desired assignment, and the adhesive is left to cure, such that all components 10, 11, 30, 4 are permanently connected to one another.

A further variant of the invention comprises the embodiment in which the alignment device 4 is formed without a base on the lower side. The alignment device 4 is formed here as a frame with support faces for the structural components 10 and guide elements 30 placed above and below. The frame is peripheral with an enclosed opening, which is completed by the leaf springs 10, 30 to form a cavity, into which adhesive 5 is introduced, such that the lower side of the upper structural component 10 and the upper side of the guide element 30 are wetted with adhesive 5 opposite one another and are adhesively bonded to one another at the alignment device 4. Both leaf springs 10, 30 are pressed against the relevant support face and are held pressed until the adhesive 5 has cured, the formed cavity is sealed by pressing against the support faces, excess adhesive 5 exits only through the outlet channel arranged in a spacer, preferably via an outlet device, and therefore the component is not contaminated by adhesive 5. Otherwise, the setup corresponds to that in FIG. 8.

Due to the above-described method, which is also part of the invention, and the orthopedic component according to the invention it is possible to adhesively bond two structural components such as leaf springs, in particular two fiber composite materials, using a liquid adhesive and at the same time to surround these structural components in order to thus provide a protective casing. The alignment device fits on or to the components to be connected and forms a cavity therebetween which forms the receiving space for the liquid adhesive. In order to introduce the adhesive into the cavity or the hollow space and at the same time ventilate the cavity, relatively small openings in the form of feed channels or outlet channels are integrated into the alignment device or the mold and casing. Tube connectors can be inserted into these feed connections and outlet channels and can be connected to a feed tube and a venting tube. In order to ensure that the cavity or the hollow space is reliably sealed, the structural components can be pressed together or can be pressed against the receiving device 4, wherein this can be made possible due to flexible materials. The material of the alignment device 4 is preferably a flexible, resilient material, such that a sealing abutment against the structural components can be ensured by exerting pressure in the direction of the structural components. Once the adhesive has been introduced and cured, the tube connectors are removed from the alignment device or the molding shell and the connection method is complete. The mold now no longer serves as a delimitation for the adhesive; it is used as a shell or casing of the structural components in order to protect the structural components against damage and additionally in order to protect further parts, for example a casing or cosmetic means against damage by the structural components connected to one another, which can have sharp edges.

Due to the device and the method it is possible to provide a mold for a liquid adhesive for the connection of two structural components. The alignment of the components to be connected is ensured by the alignment device 4, and the component parts to be connected are also protected, the production method is clean, and there is no need for any post-processing of the joint area. The consumption of adhesive is limited, since no excess adhesive can escape, and a defined volume provided by the respective cavities can serve as a basis for the calculation of the fed adhesive quantity. A quantity-controlled feed of adhesive thus ensures that, on the one hand, a minimal quantity of adhesive is used and on the other hand sufficient adhesive is always provided in order to completely fill the cavity.

The invention claimed is:

1. A prosthetic foot comprising:
    a structural component comprising a leaf spring and a proximal connection member to fasten the prosthetic foot to a below knee tube, a below knee shank, or a prosthetic knee joint, the leaf spring including:
        a support portion extending from the proximal connection member in a posterior direction;
        a connection portion connected to the support portion, wherein the leaf spring forms an arc between the support portion and the connection portion; and
        a forefoot portion connected to the connection portion;
    a sole-side guide element provided as a separate and distinct piece from the forefoot portion, connected to the forefoot portion and movable relative to the structural component about an axis arranged perpendicular to a length dimension of the guide element;
    a rear sole structure mounted to a posterior end of the guide element, the rear sole structure having a coupling portion and a ground contact portion arranged to contact a ground surface, the coupling portion and the ground contact portion being integrally formed; and
    a heel-side spring-damper system directly and interchangeably coupled to the coupling portion of the rear sole structure, the spring-damper system being compressed at a heel strike during operation of the prosthetic foot, the spring-damper system being supported on the guide element, the spring-damper system being arranged between a lower side of the structural component and an upper side of the guide element and being replaceable to provide different amounts of dampening;
    wherein the arc projects beyond the guide element in the posterior direction;
    wherein energy influx into the prosthetic foot upon heel-strike is stored in at least the heel-side spring-damper system.

2. The prosthetic foot as claimed in claim 1, wherein the arc projects beyond a natural ankle position in the posterior direction, wherein in the natural ankle position, an apex of the arc lies posteriorly behind a posterior, rear end of the sole-side guide element.

3. The prosthetic foot as claimed in claim 1, wherein the guide element is configured as a leaf spring in a forefoot of the prosthetic foot.

4. The prosthetic foot as claimed in claim 1, wherein the guide element comprises a leaf spring.

5. The prosthetic foot as claimed in claim 1, wherein the spring-damper system comprises a foam-material element or an elastomeric element.

6. The prosthetic foot as claimed in claim 1, wherein the rear sole structure includes a sole element comprising an elastic material arranged at a lower side of the guide element.

7. The prosthetic foot as claimed in claim 1, wherein the forefoot portion comprises at least one leaf spring.

8. The prosthetic foot as claimed in claim 1, wherein an overload stop is arranged between the guide element and the structural component.

9. The prosthetic foot as claimed in claim 1, wherein the guide element is mounted in a non-displaceable manner about at least one of an axis extending in an anterior-posterior direction and an axis extending in a proximal-distal direction.

10. The prosthetic foot as claimed in claim 1, wherein a heel of the prosthetic foot comprises a convex arch at a free end of the guide element.

11. The prosthetic foot as claimed in claim 1, wherein the structural component has an elastic and monolithic design.

12. The prosthetic foot as claimed in claim 1, wherein the coupling portion of the rear sole structure includes a form-fit element for fixing the spring-damper system at a posterior end of the guide element.

13. The prosthetic foot as claimed in claim 1, wherein the arc extends beyond the spring-damper system in an anterior-posterior direction by a section which is between 10% and 30% of a foot length FL.

14. The prosthetic foot as claimed in claim 1, wherein a contour-forming cushioning is arranged at a top side of the structural component in the forefoot portion.

15. The prosthetic foot as claimed in claim 1, wherein, from the proximal connection member, the structural component is concavely curved in the arc, has a convex curvature with a larger radius of curvature as compared to the arc in the support portion of the spring-damper system, and, following the larger radius of curvature, is concave in the forefoot portion.

16. The prosthetic foot as claimed in claim 1, wherein the guide element comprises a leaf spring having a concave-convex-concave profile from a heel to a tip of the prosthetic foot.

17. The prosthetic foot as claimed in claim 1, wherein the forefoot portion and the guide element are coupled to each other with an alignment device.

18. The prosthetic foot as claimed in claim 17, wherein the forefoot portion and the guide element and the alignment device are adhesively bonded to one another.

19. The prosthetic foot as claimed in claim 1, wherein the prosthetic foot is configured for arrangement in a shoe.

20. The prosthetic foot as claimed in claim 1, wherein the guide element has a film hinge.

21. The prosthetic foot as claimed in claim 1, wherein the guide element is thinner than the leaf spring and a swivel joint is provided at the connection between the guide element and the forefoot portion, and the reduced thickness of the guide element relative to the thickness of the leaf spring and the swivel joint contribute to limiting transfer of energy from the guide element into the forefoot portion of the structural component upon heel-strike.

22. The prosthetic foot as claimed in claim 1, further comprising a form-fit element fixed to the structural component to interchangeably couple the spring-damper system to a lower side of the structural component.

23. A prosthetic foot, comprising:
a sole-side guide element;
a proximal connection member configured to fasten the prosthetic foot to a lower leg prosthetic component;
a structural component connected to the guide element, the structural component comprising a leaf spring that extends from the proximal connection member in a posterior direction, forms an arc, and extends in anterior and distal directions, wherein the arc projects beyond the guide element in the posterior direction, the leaf spring having a thickness that is greater than a thickness of the guide element;
a forefoot portion connected to the structural component;
a rear sole structure mounted to a posterior end of the guide element, the rear sole structure having a coupling portion and a ground contact portion arranged to contact a ground surface, the coupling portion and the ground contact portion being integrally formed; and
a heel-side spring-damper system directly and interchangeably coupled to the coupling portion of the rear sole structure, the spring-damper system supporting itself on the guide element and being compressible at a heel strike during operation of the prosthetic foot, the spring-damper system being arranged between a lower side of the structural component and an upper side of the guide element and being replaceable to provide different amounts of dampening;
wherein the reduced thickness of the guide element relative to the thickness of the leaf spring contributes to a limited transfer of moments from the guide element to the forefoot portion upon heel strike.

24. The prosthetic foot as claimed in claim 23, wherein the coupling portion of the rear sole structure includes a form-fit element fixed to the posterior end of the guide element.

25. The prosthetic foot as claimed in claim 23, further comprising a form-fit element fixed to the structural component to interchangeably couple the spring-damper system to a lower side of the structural component.

\* \* \* \* \*